(12) United States Patent
Keene et al.

(10) Patent No.: US 9,657,852 B2
(45) Date of Patent: May 23, 2017

(54) FLOW THROUGH ISOLATION VALVE FOR HIGH PRESSURE FLUIDS

(71) Applicant: Waters Technologies Corporation, Milford, MA (US)

(72) Inventors: Russell Keene, Sudbury, MA (US); David R. Friswell, Upton, MA (US)

(73) Assignee: Waters Technologies Corporation, Milford, MA (US)

( * ) Notice: Subject to any disclaimer, the term of this patent is extended or adjusted under 35 U.S.C. 154(b) by 24 days.

(21) Appl. No.: 13/973,228

(22) Filed: Aug. 22, 2013

(65) Prior Publication Data

US 2013/0340509 A1    Dec. 26, 2013

Related U.S. Application Data

(62) Division of application No. 10/598,072, filed as application No. PCT/US2005/006764 on Mar. 2, 2005, now Pat. No. 8,539,982.

(Continued)

(51) Int. Cl.
*F16K 11/085*      (2006.01)
*F16K 5/04*      (2006.01)
(Continued)

(52) U.S. Cl.
CPC ........ *F16K 11/0853* (2013.01); *F16K 5/0428* (2013.01); *F16K 11/076* (2013.01);
(Continued)

(58) Field of Classification Search
USPC ......... 137/625.47; 251/149.9, 159, 160, 180, 251/181
See application file for complete search history.

(56) References Cited

U.S. PATENT DOCUMENTS 2,437,139 A    3/1948   Tucker
2,846,121 A    8/1958   Ronnebeck
(Continued)

FOREIGN PATENT DOCUMENTS

GB    2 290 283 A    12/1995
JP      4722742 B      6/1972
(Continued)

OTHER PUBLICATIONS

JapaneseTranslation of Notice of Rejection (Official Action); Mailing date of Nov. 22, 2010, for Patent Application No. 2007-501947; 4 pages.
(Continued)

*Primary Examiner* — John Fox
(74) *Attorney, Agent, or Firm* — Waters Technologies Corporation

(57) ABSTRACT

A flow through isolation valve having a stationary member; a movable member, with a surface of the stationary member interfacing with a surface of the movable member; and at least one pin isolation valve. The pin isolation valve has a flow through internal conduit and is movable so that the internal conduit can fluidically communicate with at least one blank opening in the movable member and with a flow through internal conduit in the movable member. Movement is by rotation, linear or curvilinear translation. At least one pin isolation valve is fluidically coupled typically to a sample loop of a face seal valve, or to a pump supplying high pressure liquid to or to a column discharging liquid from a face seal valve of a high pressure liquid chromatography (HPLC) system or directly to the face seal valve.

9 Claims, 13 Drawing Sheets

Related U.S. Application Data

(60) Provisional application No. 60/550,923, filed on Mar. 5, 2004.

(51) Int. Cl.
*F16K 11/076* (2006.01)
*G01N 30/28* (2006.01)

(52) U.S. Cl.
CPC ...... *G01N 30/28* (2013.01); *Y10T 137/86863* (2015.04); *Y10T 137/86871* (2015.04); *Y10T 137/87161* (2015.04)

(56) References Cited

U.S. PATENT DOCUMENTS

| | | | |
|---|---|---|---|
| 2,972,888 A | | 2/1961 | Larnkin |
| 3,098,506 A | | 7/1963 | Spragens |
| 3,119,251 A | | 1/1964 | Bowers |
| 3,192,968 A | * | 7/1965 | Baruch et al. ............... 141/82 |
| 3,201,922 A | | 8/1965 | Villalobos |
| 3,530,721 A | | 9/1970 | Hirdina et al. |
| 3,630,371 A | | 12/1971 | Hrdina et al. |
| 3,683,701 A | | 8/1972 | Gunther et al. |
| 3,698,428 A | | 10/1972 | Gastin |
| 3,744,512 A | | 7/1973 | Billman |
| 4,102,782 A | | 7/1978 | Saito et al. |
| 4,346,610 A | | 8/1982 | Ishii et al. |
| 4,394,263 A | | 7/1983 | Dosch et al. |
| 4,454,749 A | | 6/1984 | Guillemin et al. |
| 4,602,657 A | | 7/1986 | Anderson, Jr. et al. |
| 4,655,095 A | | 4/1987 | Russo et al. |
| 4,792,396 A | * | 12/1988 | Gundelfinger ............ 210/198.2 |
| 5,419,208 A | * | 5/1995 | Schick ....................... 73/863.73 |
| 8,196,896 B2 | | 6/2012 | Keene |
| 8,539,982 B2 | | 9/2013 | Keene et al. |
| 2008/0190498 A1 | | 8/2008 | Keene et al. |

FOREIGN PATENT DOCUMENTS

| | | |
|---|---|---|
| JP | 53-030390 A | 3/1978 |
| JP | 55144543 | 11/1980 |
| JP | 58217868 | 12/1983 |
| JP | 59-195565 U | 12/1984 |
| JP | 60-004956 U | 1/1985 |
| JP | 60-090673 U | 6/1985 |
| JP | 61166279 U | 10/1986 |
| JP | 04-051660 U | 4/1992 |
| JP | 04-297866 A | 10/1992 |
| JP | 05-023130 U | 3/1993 |
| JP | 08-005621 A | 1/1996 |
| JP | 2000-186985 A | 7/2000 |

OTHER PUBLICATIONS

JapaneseTranslation of Notice of Rejection (Official Action); Mailing date of Jan. 10, 2012, for Patent Application No. 2007-501947; 4 pages.
PCT International Search Report for PCT/US2005/06764, mailing date of Jan. 18, 2006, 4 pages.
PCT International Written Opinion for PCT/US2005/06764, mailing date of Jan. 18, 2006, 5 pages.
PCT International Preliminary Report on Patentability for PCT/US05/06764, mailing date of Sep. 5, 2006, 5 pages.
Translation of Notice of Rejection for Japanese Patent Application No. 2007-501947, drafting date: Dec. 28, 2011, 7 pages.
Japanese Search Report for Application No. 2012-153714, issued Sep. 13, 2013 (17 pages).

* cited by examiner

FLOW THROUGH ISOLATION VALVE FOR HIGH PRESSURE FLUIDS

CROSS REFERENCE TO RELATED APPLICATIONS

This application is a divisional of U.S. application Ser. No. 10/598,072 filed on Mar. 28, 2008, which is the National Stage of International Application No. PCT/US05/06764 filed on Mar. 2, 2005, which claims priority to and benefit of U.S. Provisional Patent Application No. 60/550,923, filed Mar. 5, 2004. The entire contents and teachings of each of these applications are hereby expressly incorporated herein by reference in their entirety.

BACKGROUND OF THE INVENTION

The invention relates generally to the field of high pressure fluids and, more specifically, to an isolation valve that permits introduction of an alternate flow path without interruption of flow from the fluid source.

DESCRIPTION OF RELATED ART

Conventional 6-port face shear valves, also referred to as face seal valves, used in high pressure liquid chromatography (HPLC) provide ports that interface with the sample, the syringe, the pump, the column and the two ends of the sample loop. Such face seal valves must be rotated to switch from one port to another. The rotation of the face seal under high pressure inherently causes damage to the plastic mating surfaces because the fluid port openings must slide against the rotor surface causing fatigue of the rotor material. This results in shortened face seal valve life.

What is needed is an intermediary isolation valve that protects the face seal valve so that it will not be required to switch or rotate under high pressure. The isolation valve should not cause stoppage of flow during switching, and therefore should provide a substantially uniform, non-disrupted fluid introduction flow path.

BRIEF SUMMARY OF THE INVENTION

To address the above and other issues, the present invention describes a flow-through high pressure isolation valve for high pressure fluids, and which is particularly suitable for use in HPLC applications.

It is an object of this invention to minimize the face damage inherent in face-shear valves at high pressure because the fluid port openings do not slide against The rotor surface causing fatigue of the rotor material. Therefore valve life when switching high pressure fluids is greater.

At higher chromatography pressures (>15,000 psig or 100 MPa), the flow-through isolation valve can be used to protect a conventional "flow-through isolation" inject valve so that it does not have to switch (turn) at high pressure.

In a particular aspect of the invention, the present invention is directed to a flow through isolation valve, the flow through isolation valve comprising: a stationary member; a movable member, a surface of the stationary member interfacing with a surface of the movable member; and at least one pin isolation valve. The at least one pin isolation valve has a flow through internal conduit, and is movably disposed so that the internal conduit is capable of fluidically communicating with at least one blank opening in the movable member, and is movably disposed so that the internal conduit within the pin isolation valve is capable of fluidically communicating with a flow through conduit in the movable member. The movable member moves by rotation around an axis of rotation or by at least one of linear and curvilinear translation. At least one pin isolation valve can be fluidically coupled to a sample loop of a face seal valve of a high pressure liquid chromatography (HPLC) system or fluidically coupled to a pump supplying high pressure liquid to a face seal valve of a HPLC system or fluidically coupled to a column discharging high pressure liquid from a face seal valve of a HPLC system.

In a specific aspect of the invention, the present invention is directed to a flow though isolation valve, the isolation valve disposed around an axis of rotation, and comprises: at least two opposing valve ends disposed around the axis of rotation; a rotor disposed between the valve ends, with an axis of rotation of the rotor being substantially one of parallel and coincident with the axis of rotation of the isolation valve, and the rotor is disposed such that orientation of the rotor can change by rotation around the axis of rotation of the rotor. The rotor has an outer surface having at least first and second openings on the outer surface, at least two surfaces each intersecting the outer surface. A first flow-through conduit has an opening on a first of the at least two surfaces intersecting the outer surface and an opening on a second of the at least two surfaces intersecting the outer surface; and an opening on the outer surface coincident with the first opening on the outer surface and an opening on the first of the at least two surfaces intersecting the outer surface. A second flow through conduit has an opening on the outer surface coincident with the second opening on the outer surface and an opening on the second of the at least two surfaces intersecting the outer surface. There is at least one blank opening on the first of the at least two surfaces intersecting the outer surface, at least one blank opening on the second of the at least two surfaces intersecting the outer surface, with a first sealing annulus for sealing the openings on the first of the at least two surfaces intersecting the outer surface, and a second sealing annulus for sealing the openings on the second of the at least two surfaces intersecting the outer surface. The flow through isolation valve also has a first pin isolation valve having an internal conduit, with the first pin isolation valve disposed to move along the axis of rotation of the isolation valve through one of the valve ends; and movably disposed so that the internal conduit is capable of fluidically communicating with the at least one blank opening on the first of the at least two surfaces intersecting the outer surface, and movably disposed so that the internal conduit is capable of fluidically communicating with the flow through conduit having an opening on the outer surface and an opening on a second of the at least two surfaces intersecting the outer surface. The flow through isolation valve also includes a second pin isolation valve, with the second pin isolation valve disposed to move along the axis of rotation of the isolation valve through another one of the valve ends, the pin isolation valve including an internal conduit; and movably disposed so that the internal conduit is capable of fluidically communicating with the at least one blank opening on the second of the at least two surfaces intersecting the outer surface, and movably disposed so that the internal conduit within the second pin isolation valve is capable of fluidically communicating with the flow through conduit having an opening on the outer surface and an opening on the second of the at least two surfaces intersecting the outer surface.

The axis of rotation of the rotor can be the centerline of the rotor and the axis of rotation of the isolation valve can be the centerline of the isolation valve. The rotor can further comprise: a rotor clamp having an outer surface and an inner surface, with the inner surface surrounding at least a portion of the outer surface of the rotor, a first opening on the outer surface of the rotor clamp penetrating the rotor clamp to coincide with the first opening on the outer surface of the rotor, and a second opening on the outer surface of the rotor clamp penetrating the rotor clamp to coincide with the second opening on the outer surface of the rotor. The flow through isolation valve can further comprise at least one of a (a) third pin isolation valve, and (b) fourth pin isolation valve. The third pin isolation valve has an internal conduit, and is disposed within the first opening on the outer surface of the rotor clamp so that the internal conduit of the third pin isolation valve is disposed to be in fluidic communication with the opening on the outer surface of the flow through conduit having an opening on the outer surface and an opening on the first of the at least two surfaces intersecting the outer surface of the rotor. The fourth pin isolation valve has an internal conduit, and is disposed within the second opening on the outer surface of the rotor clamp so that the internal conduit of the fourth pin isolation valve is disposed to be in fluidic communication with the opening on the outer surface of the flow through conduit having an opening on the outer surface and an opening on the second of the at least two surfaces intersecting the outer surface of the rotor.

The rotor clamp can further comprise drive means for driving the rotor to rotate around the axis of rotation of the rotor. The drive means can comprise a gear drive operator or a handle operator. At least one of the valve ends comprises typically: a stator enclosing the at least one pin isolation valve, with the stator adjacent to the rotor; a sealing layer enclosed within the stator and enclosing the at least one pin isolation valve for sealing the at least one pin isolation valve; a Belleville spring washer; a Belleville spring; a load washer; and a spherical nut, the Belleville spring washer, the Belleville spring, the load washer and the spherical nut axially arranged to impose an axial force for sealing the sealing layer enclosing the pin isolation valve.

In an alternate embodiment, the flow through isolation valve comprises a stationary member; and a movable member. The stationary member and the movable member interface at a surface, with the movable member disposed to slide along the surface; and a chamber is disposed between the stationary member and the movable member. The chamber is bounded by the surface; and the movable member has a first flow through conduit having an opening interfacing with the chamber and an opening on a surface of the movable member not interfacing with the chamber; and a second flow through conduit having an opening interfacing with the chamber and an opening on a surface of the movable member not interfacing with the chamber, with a first blank opening on the surface bounding the chamber, and a second blank opening on the surface bounding the chamber. The flow through isolation valve can further comprise: a first pin isolation valve having an internal conduit, with the first pin isolation valve disposed within the opening of the first flow through conduit on a surface of the movable member not interfacing with the chamber, with the internal conduit of the first pin isolation valve for f fluidically communicating with the first flow through conduit; and a second pin isolation valve having an internal conduit, with the second pin isolation valve disposed within the opening of the second flow through conduit on a surface of the movable member not interfacing with the chamber, with the internal conduit of the second pin isolation valve for fluidically communicating with the second flow through conduit.

The flow through isolation valve can further comprise at least one of a (a) third pin isolation valve, and (b) fourth pin isolation valve. The third pin isolation valve has an internal conduit, and is disposed within an opening within the stationary member interfacing with the chamber so that the internal conduit of the third pin isolation valve is movably disposed to be in fluidic communication with the opening interfacing with the chamber and an opening on a surface of the stationary member not interfacing with the chamber, and the internal conduit is movably disposed to be in fluidic communication with the first blank opening on the surface bounding the chamber. The fourth pin isolation valve has an internal conduit, and is disposed within an opening within the stationary member interfacing with the chamber so that the internal conduit of the fourth pin isolation valve is movably disposed to be in fluidic communication with the opening interfacing with the chamber and an opening on a surface of the stationary member not interfacing with the chamber, the internal conduit of the fourth pin isolation valve movably disposed to be in fluidic communication with the second blank opening on the surface bounding the chamber. The flow through isolation valve can further comprise a housing enclosing the stationary member and the movable member or a housing enclosing the stationary member and the movable member and at least one of the pin isolation valves, the internal conduit of the at least one pin isolation valve fluidically coupled to a conduit penetrating the housing. At least one of the openings of the third and fourth pin isolation valves is sealed by a lip seal. The lip seal preferably is self-energizing. The movable member consists of at least one of (a) metal, (b) polymer, and (c) sapphire.

In a method of operating the flow through isolation valve, the valve comprises: a movable member, with the movable member having first and second conduits for interfacing with internal conduits of first and second pin isolation valves. The internal conduits open to a surface of the movable member; with first and second blank openings for interfacing with the internal conduits of the first and second pin isolation valves, (A) wherein the valve is in an initial position of flow isolation such that at least one of (a) the first pin isolation valve providing fluid flow interfaces with the first blank opening and (b) the second pin isolation valve exhausting the fluid flow interfaces with the second blank opening, the method comprises the steps of: (I) wherein the first pin isolation valve interfaces with the first blank opening, (1) moving said first pin isolation valve away from the first blank opening, (2) moving the movable member, and (3) moving the first pin isolation valve towards the movable member such that the internal conduit within the first pin isolation valve interfaces with the first conduit opening to a surface of the movable member; and (II) wherein the second pin isolation valve interfaces with the second blank opening, (1) moving the second pin isolation valve away from the second blank opening, (2) moving the movable member, and (3) moving the second pin isolation valve towards the movable member such that the internal conduit within the second pin isolation valve interfaces with the second conduit opening to a surface of the movable member. In (B) wherein the valve is in an initial position of flow throughput such that at least one of (a) the first pin isolation valve providing fluid flow interfaces with the first conduit and (b) the second pin isolation valve exhausting the fluid flow interfaces with the second conduit, the method comprises the steps of: (III) wherein the first pin isolation valve interfaces with the first conduit, (1) moving the first pin isolation valve away from the first conduit, (2) moving the movable member, and (3) moving the first pin isolation valve towards the movable member such that the internal conduit within the first pin isolation valve interfaces with the first blank opening; and (IV) wherein the second pin isolation valve interfaces with the second conduit, (1) moving the second pin isolation valve away from the second conduit, (2) moving the movable member, and (3) moving the second pin isolation valve towards the movable member such that the internal conduit within the second pin isolation valve interfaces with the second blank opening.

The method can be applied wherein the flow through isolation valve supplies fluid flow to a high pressure liquid chromatography (HPLC) system, wherein the system comprises the flow through isolation valve, and a face seal valve, with the face seal valve having a first port for receiving high pressure fluid, a second port capable of being fluidically coupled to at least one of the first port and to an inlet end of a sample loop, a third port capable of being fluidically coupled to a sample supply and to at least one of the inlet end of the sample loop and to a fourth port capable of being fluidically coupled to a syringe for aspirating the sample, a fifth port capable of being fluidically coupled to at least one of the fourth port and to an outlet end of the sample loop, and to a sixth port for discharging high pressure fluid, the flow through isolation valve fluidically coupled to the face seal valve by means of a first conduit coupling the first port and the first conduit and by means of a second conduit coupling the sixth port and the second conduit, the method further comprises the steps of: (A') during a load phase wherein the flow through isolation valve is in an initial position of flow isolation: (1') coupling the second port to the third port, (2') coupling the fifth port to the fourth port, and (3') aspirating sample liquid into the sample loop by operating the syringe. In (B') a transition phase wherein the flow through isolation valve remains in the initial position of flow isolation, the method further comprises the steps of: (1') transferring coupling of the second port from the third port to the first port for receiving high pressure liquid, and (2') transferring coupling of the fifth port from the fourth port to the sixth port for discharging high pressure liquid. In (C') during an injection phase wherein the face seal valve is in a position of flow throughput through the sample loop and (I) wherein the first pin isolation valve interfaces with the first blank opening, the method farther comprises the steps of: (1) moving the first pin isolation valve away from the first blank opening; (2) moving the movable member; and (3) moving the first pin isolation valve towards the movable member such that the internal conduit within the first pin isolation valve interfaces with the first conduit opening to a surface of the movable member; and (II) wherein the second pin isolation valve interfaces with the second blank opening, (1) moving the second pin isolation valve away from the second blank opening; (2) moving the movable member; and (3) moving the second pin isolation valve towards the movable member such that the internal conduit within the second pin isolation valve interfaces with the second conduit opening to a surface of the movable member.

Following (C') the injection phase wherein the face seal valve is in a position of flow throughput through the sample loop, the method can further comprise the steps of:

(B) wherein the flow through isolation valve is in an initial position of flow throughput such that at least one of (a) the first pin isolation valve providing fluid flow interfaces with the first conduit and (b) the second pin isolation valve exhausting the fluid flow interfaces with the second conduit, and (III) wherein the first pin isolation valve interfaces with the first conduit, (1) moving the first pin isolation valve away from the first conduit; (2) moving the movable member; and (3) moving the first pin isolation valve towards the movable member such that the internal conduit within the first pin isolation valve interfaces with the first blank opening; and (IV) wherein the second pin isolation valve interfaces with the second conduit, (1) moving the second pin isolation valve away from the second conduit; (2) moving the movable member; and (3) moving the second pin isolation valve towards the movable member such that the internal conduit within the second pin isolation valve interfaces with the second blank opening.

Following (B') the transition phase wherein the face seal valve is in a position of flow throughput through the sample loop, the method can further comprise the steps of:

(1'') transferring coupling of the fifth port from the sixth port to the fourth port, and (2'') transferring coupling of the second port from the first port to the third port. and the step of: (3'') aspirating sample liquid into the sample loop by operating the syringe. The method can further comprise, wherein the steps (A) wherein the valve is in an initial position of flow isolation and (I) wherein the first pin isolation valve interfaces with the first blank opening, and (II) wherein the second pin isolation valve interfaces with the second blank opening, the steps of: (1) moving the first pin isolation valve away from the first blank opening and moving the second pin isolation valve away from the second blank opening are performed simultaneously; and (2) moving the movable member; so that (3) moving the first pin isolation valve towards the movable member such that the internal conduit within the first pin isolation valve interfaces with the first conduit opening to a surface of the movable member and moving the second pin isolation valve towards the movable member such that the internal conduit within the second pin isolation valve interfaces with the second conduit opening to a surface of the movable member are performed simultaneously. The method can further comprise, wherein the steps (B) wherein the valve is in an initial position of flow throughput and (III) wherein the first pin isolation valve interfaces with the first conduit, and (IV) wherein the second pin isolation valve interfaces with the second conduit, the steps of: (1) moving the first pin isolation valve away from the first conduit and moving the second pin isolation valve away from the second conduit are performed simultaneously, and (2) moving the movable member, so that (3) moving the first pin isolation valve towards the movable member such that the internal conduit within the first pin isolation valve interfaces with the first blank opening and moving the second pin isolation valve towards the movable member such that the internal conduit within the second pin isolation valve interfaces with the second blank opening are performed simultaneously.

BRIEF DESCRIPTION OF THE DRAWINGS

These and other features, benefits and advantages of the present invention will become apparent by reference to the following text and figures, with like reference numbers referring to like structures across the views, wherein.

DETAILED DESCRIPTION OF THE INVENTION

This application incorporates by reference concurrently filed provisional application Ser. No. 60/550,930.

The present invention describes an isolation valve and rotor for use in high pressure fluid systems that permits switching to another flow path without temporarily blocking flow as would occur in face-shear valves as are customarily used in high pressure fluid systems, in particular in high pressure liquid chromatography. The valve and rotor allow for high pressure injections from a face-shear valve to a column without disrupting fluid flow. The sample fluid injection circuit may be isolated from the remainder of the HPLC system. The isolation valve includes a housing having a bore therethrough and a cylindrical rotor rotatable within the bore.

The bore wall includes two axially spaced holes. The first hole serves as an input to the sample injector or valve and the second hole serves as an outlet from the sample injector or valve. The rotor includes a first end for delivering fluid from a pump and a second end for receiving fluid from the sample circuit.

On the outer surface of the rotor are a first port for receiving fluid from the pump, the port being fluidically coupled to the first end for delivering fluid from the pump, and a second port for delivering the fluid received from the sample circuit to a HPLC column, the second port being fluidically coupled to the second end for receiving fluid from the sample circuit. The rotor also includes a pair of axially spaced ports that register with the first and second ports of the housing bore when the rotor is positioned in a fluid flow position. Although the ports are preferably offset by an angle of about 90° from each other on the outer surface of the rotor, the ports can be aligned to be adjacent to each other.

A bore that is typically at right angles extends in the rotor between the first end and the first port of the pair of axially spaced ports of the rotor and another bore that is typically at right angles extends in the rotor between the second end and the second port of the pair of axially spaced ports of the rotor. Both the first end and second end of the rotor are each further provided with an axially spaced fluid stop port positioned preferably at a 45' angle relative to the pair of axially spaced ports.

When the rotor is in its fluid flow position, fluid flows from a pump, through the isolation valve, to the sample injector circuit, back through another portion of the valve, and then to a column. By turning the rotor preferably 90°, the fluid stop ports prevent the flow of fluid and isolate the sample circuit from the remainder of the HPLC system.

Figure 1A:
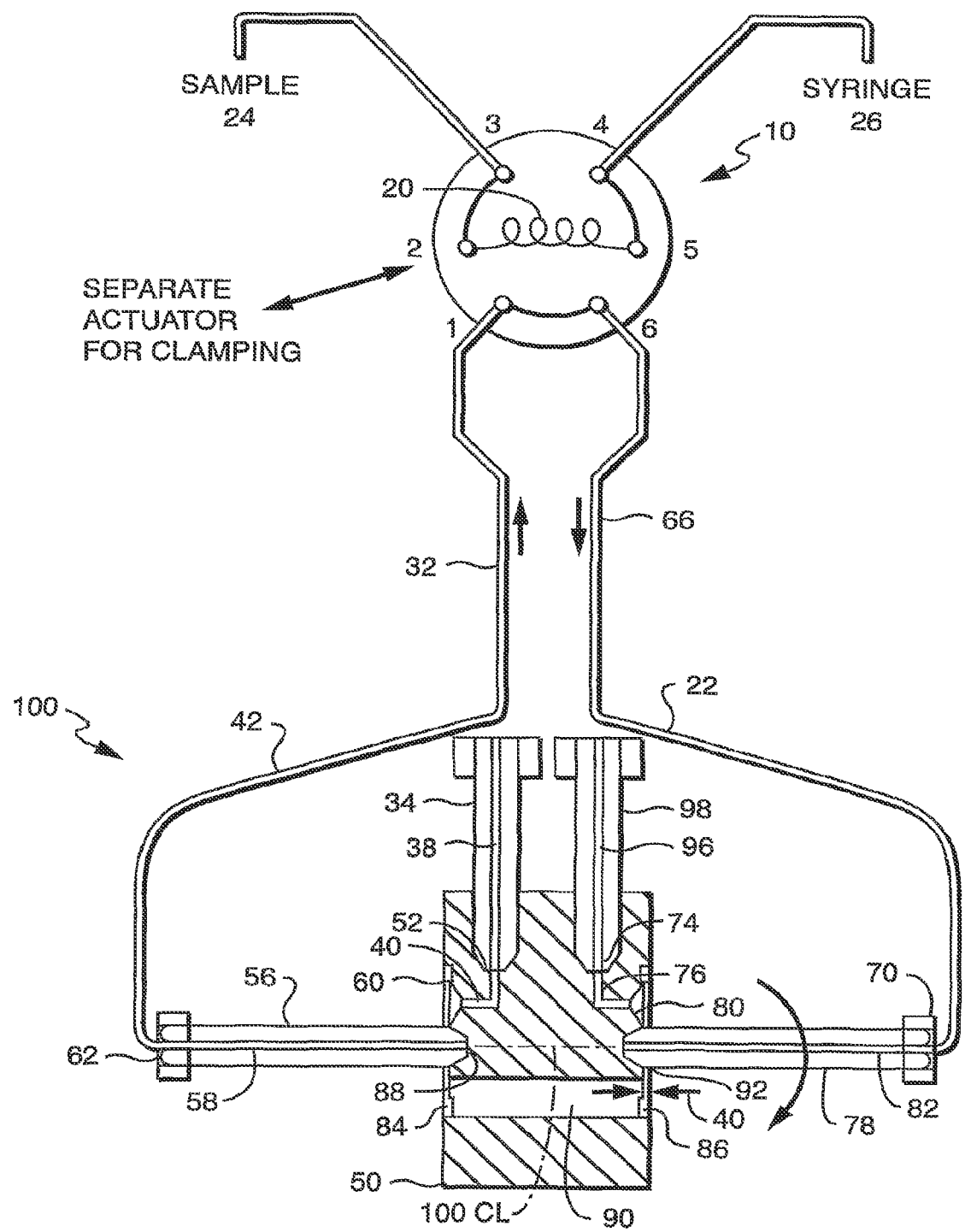
FIG. 1A illustrates a partial embodiment of the flow-through isolation valve of the present invention in a load phase as it interfaces with a face seal valve.

In particular, in FIG. 1A, a conventional face seal valve 10 has six ports 1, 2, 3, 4, 5 and 6. As shown, port 1 is supplied from the high pressure pump (not shown), port 2 interfaces with one end of sample loop 20 such that the other end of the loop 20 interfaces with port 5. Port 3 interfaces with a sample supply tube 24 while port 4 interfaces with syringe tube 26. Port 6 is coupled to the HPLC capillary column (not shown). The face seal valve 10 rotates clockwise or counterclockwise to switch between adjacent port connections as is known to those skilled in the art. In FIG. 1A, the face seal valve 10 is in the load position since sample supply tube 24 is in an interface position through port 3 which is fluidically coupled through port 2 with one end of the loop 20. The other end of the loop 20 is fluidically coupled through port 5 and port 4 to the syringe 26

In a partial embodiment of the present invention of a flow through isolation valve 100, during the load phase, the loop 20 is disconnected from high pressure fluid that otherwise flows to port 1 from conduit tubing 32. The conduit tubing 32 is preferably flexible at least along one end 42 which interfaces with internal conduit 58 within isolation valve pin 56. Coupling 62 couples the flexible tube 42 to isolation valve pin 56. During the load phase, the isolation valve pin 56 is positioned to interface with a blank port 88 on a side of a rotor 50. The rotor 50 has a centerline axis of rotation 100CL. Sample fluid is provided from a high pressure pump (not shown) through fitting 34 by way of internal conduit 38. The fitting 34 is in direct contact with rotor 50 at port 52. During the load phase, the internal conduit 38 provides high pressure fluid through internal conduit 40 within the rotor 50 to an open port 60 that is fluidically coupled to an annular passageway 84. Since the isolation valve pin 56 interfaces with the blank port 88, flow of high pressure fluid from the high pressure pump to the port 1 of the face seal valve 10 is effectively isolated.

Similarly, flow from the face seal valve 10 from port 6 would otherwise discharge to the capillary column at port 6 into conduit tubing 66. The conduit tubing 66 also is preferably flexible at least along one end 22 which interfaces with internal conduit 82 within pin isolation valve 78. Conduit tubing 66 is coupled to pin isolation valve 78 by means of coupling 70. During the load phase, the pin isolation valve 78 is positioned to interface with a blank port 92 on the opposite side of the rotor 50. Internal conduit 76 within the rotor 50 permits the flow of fluid to flow through the HPLC column isolation pin valve 98 where the internal conduit 76 fluidically couples to an internal conduit 96 within the column fitting pin 98. The internal conduit 76 has a port 80 on the same side of the rotor 50 as blank port 92. During the load phase, since the pin isolation valve 78 interfaces with the blank port 92 rather than the open port 80, flow to the HPLC column through isolation pin valve 98 is effectively isolated.

In addition to annular passageway 84, annular passageway 86 is provided on the same side of the rotor 50 as open port 80 to permit the flow of fluid from the pump directly to the column by way of internal rotor passageway 90.

Therefore, during the load phase, the flow through isolation valve 100, having effectively isolated the high pressure fluid from the high pressure pump and flow to the column, permits the face seal valve 10 to be turned freely without being subject to high pressures. Due to the high operating pressure, to prevent external leakage, the isolation valves pins 56 and 78 are rigidly inserted into ports 88 and 92 in a manner so as to substantially prevent external leakage by means known to those skilled in the art.

Figure 1B:
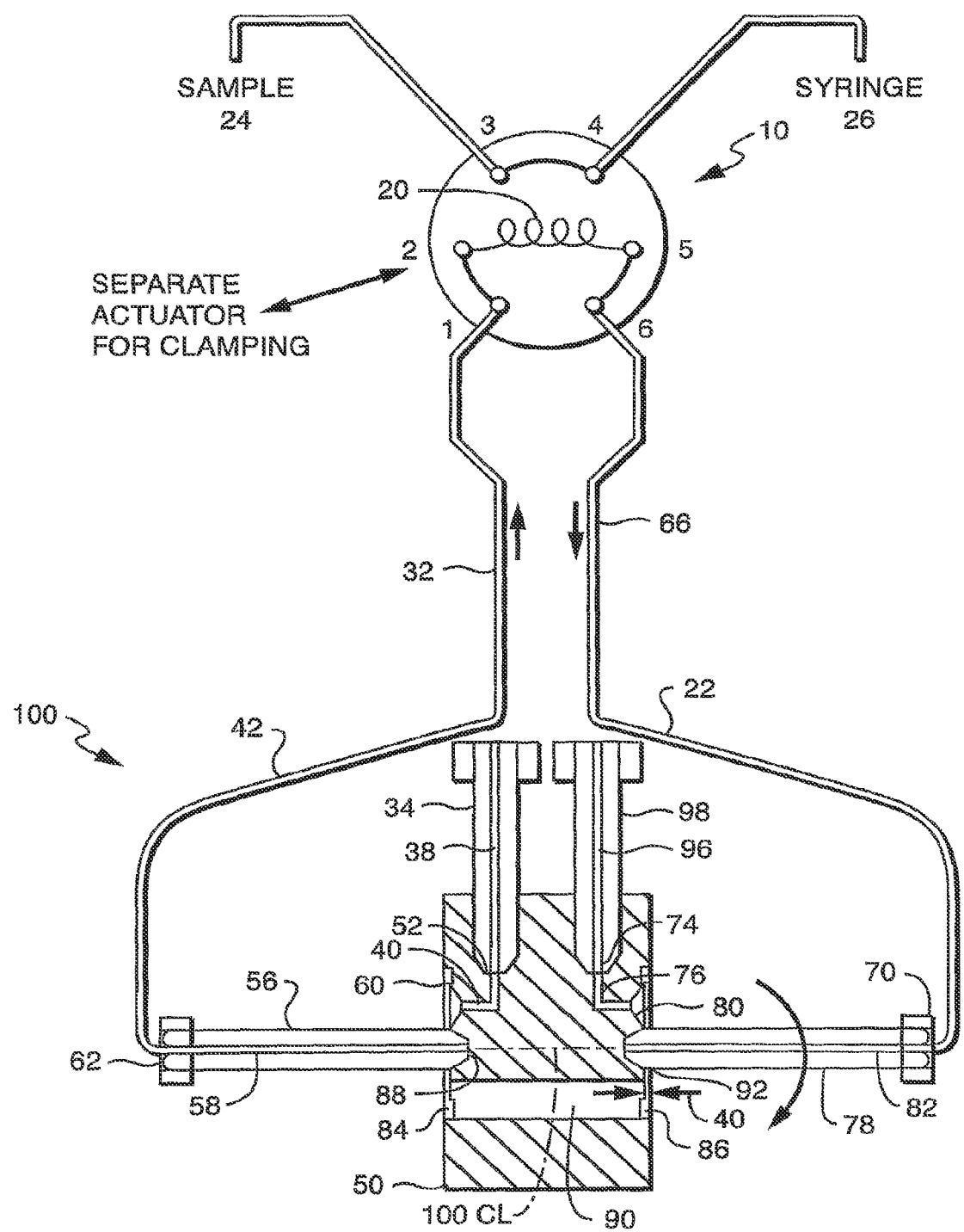
FIG. 1B illustrates a partial embodiment of the flow through isolation valve of FIG. 1A in the transition phase.

FIG. 1B illustrates a partial embodiment of the flow through isolation valve 100 in the transition phase. The transition phase is an intermediate phase between the load phase and the inject phase. During the transition phase, the position and orientation of the flow through isolation valve 100 remains the same as in the load phase described previously for FIG. 1A. However, port 1 of the face seal valve 10 is now fluidically coupled to one end of the loop 20 at port 2 while the other end at port 5 is fluidically coupled to port 6.

Figure 1C:
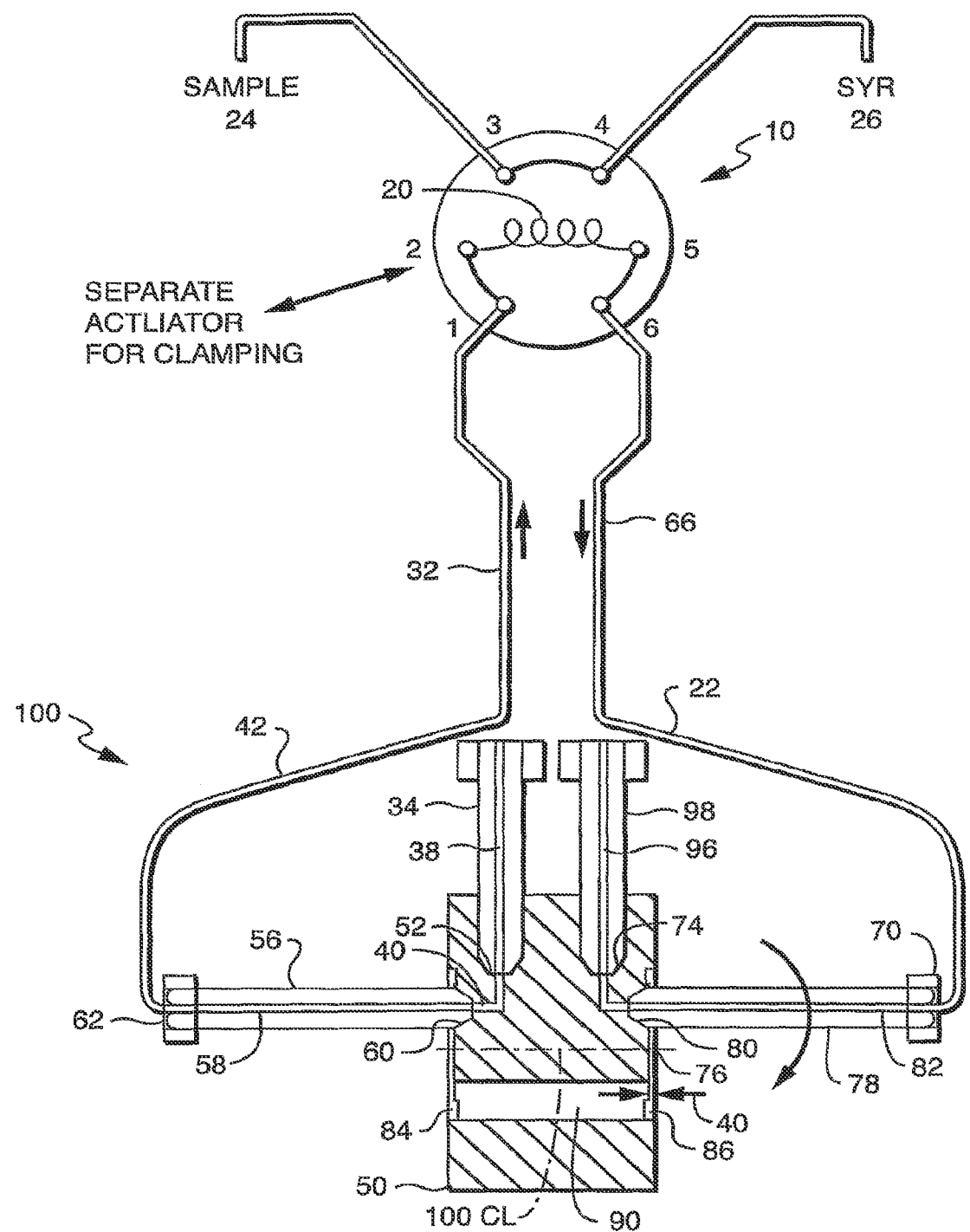
FIG. 1C illustrates a partial embodiment of the flow through isolation valve of FIG. 1A in the injection phase.

FIG. 1C illustrates a partial embodiment of the flow through isolation valve 100 in the injection phase. In the inject phase, the position and orientation of the face seal valve 10 remains the same as during the transition phase. However, the position and orientation of the flow through isolation valve 100 are changed as follows. The rotor 50 is rotated preferably 90° about the centerline axis of rotation 100CL. The isolation valve pin 56 is positioned to interface with port 60 so that internal conduit 58 within the isolation valve pin 56 is in fluidic communication with the internal conduit 40 of the rotor 50. Therefore, the high pressure liquid originating from pin isolation valve 34 is now in fluidic communication with ports 1 and 2 and the loop 20 of the face seal valve 10. Correspondingly, the isolation valve pin 78 is positioned to interface with port 80 so that internal conduit 76 within the isolation valve pin 78 is fluidically coupled with the loop 20 through ports 5 and 6 thereby enabling injection of high pressure fluid to the column through the internal conduit 96 within isolation valve pin 98.

Those skilled in the art recognize that following the inject phase illustrated in FIG. 1C, the flow through isolation valve 100 can be returned to the load phase by reversing the operation back to the transition phase illustrated in FIG. 1B and subsequently to the load phase illustrated in FIG. 1A.

Figure 2:
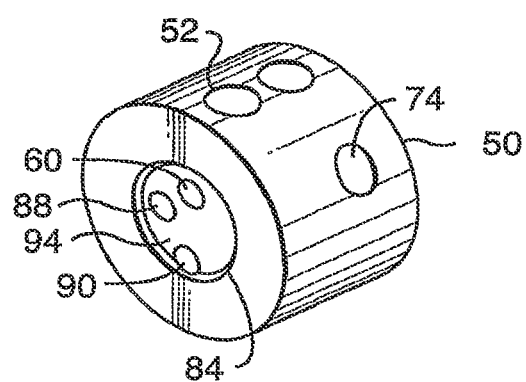
FIG. 2 is a perspective view of the rotor of the partial embodiment of the flow-through isolation valve of FIGS. 1A-1C.

FIG. 2 is a perspective view of the rotor 50 showing the ports 52 and 74 at least one of which is typically oriented on the upper portion of the outer surface of the rotor 50. Although ports 52 and 74 can be aligned on the upper portion of the outer surface of the rotor 50 to be immediately adjacent to each other, because ports 52 and 74 preferably include connections necessary to prevent external leakage and also because of the need for seals to be positioned for isolation valve pins 34 and 98, ports 52 and 74 are preferably offset from each other by 90°. Port 52 permits flow from the high pressure pump to the port 60. Corresponding port 80 on the opposite end (not shown) permits flow through the port 74 and onward to the chromatography column. The blank port 88 is provided and is typically positioned such that the angle formed by port 60, rotor center point 100CL, and blank port 88 is 90°. When the pin 56, that allows flow to the shear valve 10, port 1, is moved away from port 60, the rotor 50 can be rotated 90° so that the pin 56 can then be inserted into blank port 88, thereby isolating flow of fluid from the shear valve 10. Fluid can then circulate through the annular passageway 84 as is described later.

Figure 3A:
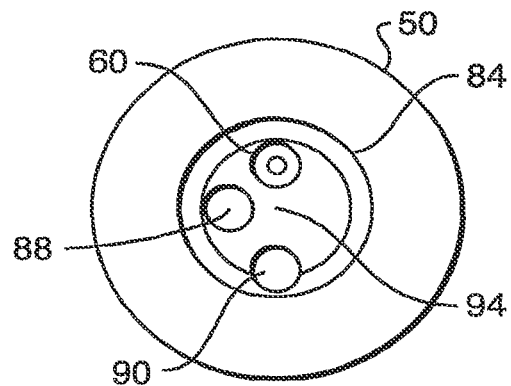
FIG. 3A is an end elevation view of the rotor of the flow-through isolation valve of FIG. 2.

FIG. 3A is an end view of the rotor 50 of FIG. 2 showing the port 60 that receives flow from the high pressure pump, the blank port 88, the internal rotor passageway 90, and the annular passageway 84.

Figure 3B:
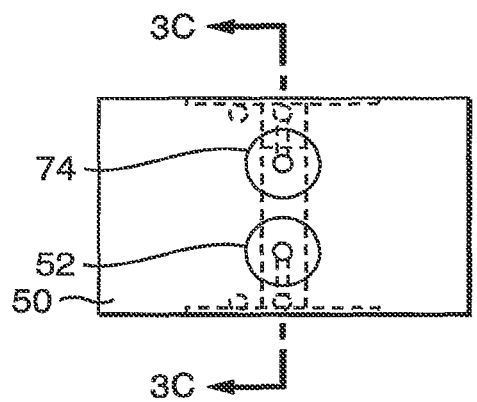
FIG. 3B is a plan view of the rotor of the flow-through isolation valve of FIG. 2.

FIG. 3B is a plan view of the rotor 50 of FIG. 2. The ports 52 and 74 appear in plan view.

Figure 3C:
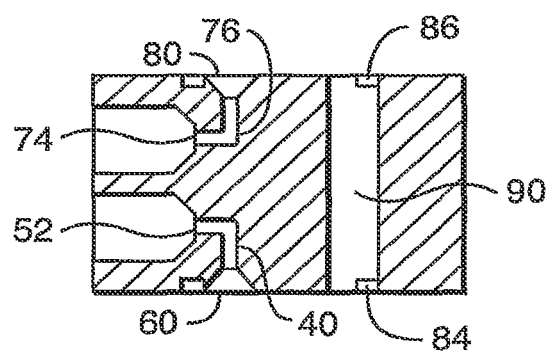
FIG. 3C is a cross-section view taken along the centerline 3C-3C' of FIG. 3C.

FIG. 3C is a cross-section view of the rotor 50 taken along the centerline 3C-3C of FIG. 3B. Ports 52 and 60 are shown coupled by internal conduit 40, while internal conduit 76 couples ports 74 and 80. Blank fluid flow stop port 88 is positioned opposite to corresponding blank fluid flow stop port 92 on the opposite end of the rotor 50. As noted previously, annular passageways 84 and 86 provided on either end of the rotor 50 to permit the flow of fluid from the pump directly to the column by way of internal rotor passageway 90. Because of continuous flow in the internal rotor passageway 90, stagnant conditions do not occur typically so it is not generally necessary to provide a wash system for the internal rotor passageway 90.

Figure 4:
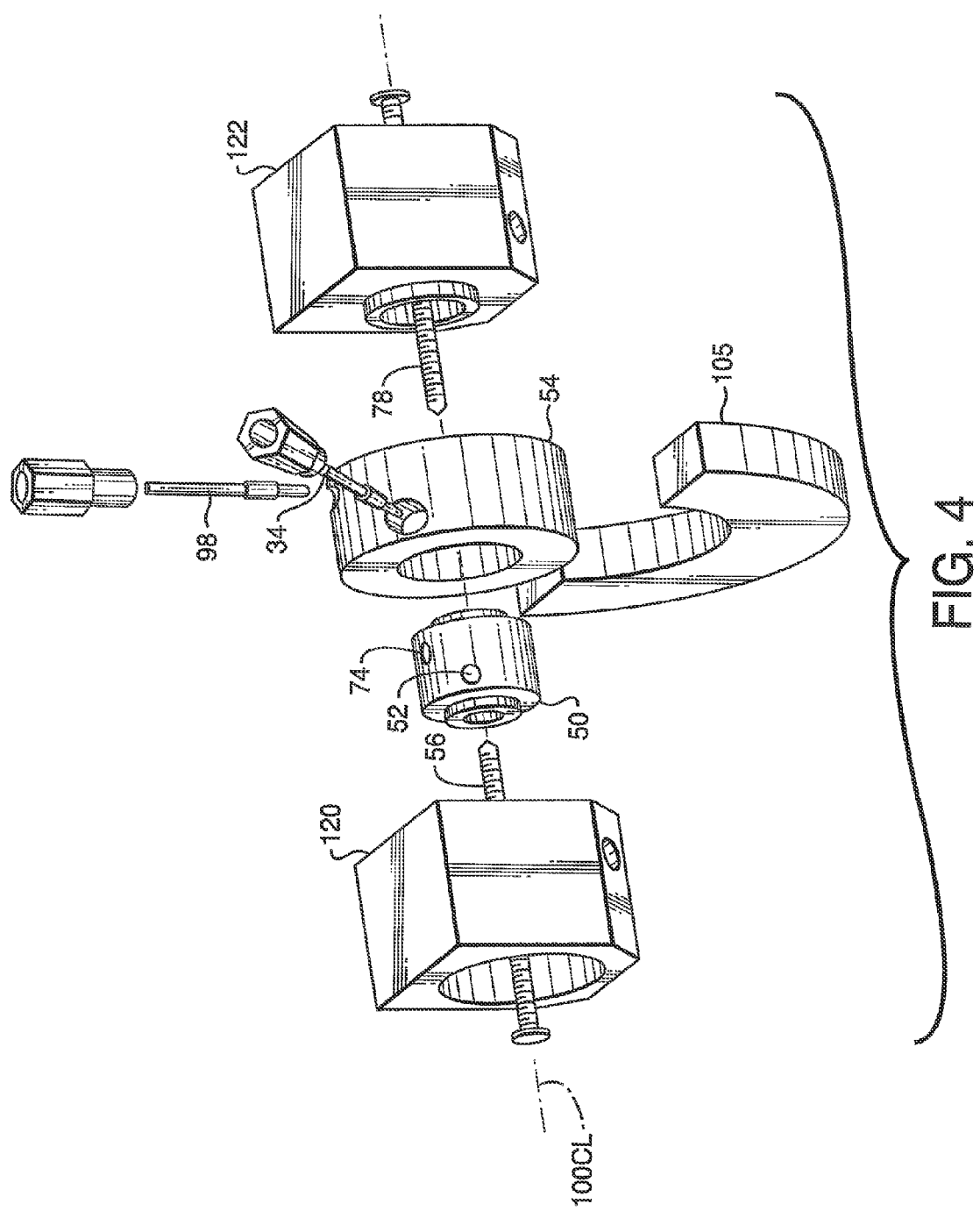
FIG. 4 is an exploded view of the rotor and stators and other components of a first variation of the partial embodiment of the flow-through isolation valve of FIGS. 1A-1C.

FIG. 4 is an exploded view of a portion of the components comprising a first variation of the embodiment of the flow through isolation valve 100. Pump supply fitting 34 interfaces with port 52 in the rotor 50 and outlet supply to column fitting 98 interfaces with port 74 in the rotor 50. Face seal valve supply pin 56 is surrounded by stator 120 and interfaces with one end of rotor 50 while face seal valve discharge pin 78 is surrounded by stator 122 and interfaces with the opposite end of rotor 50. During normal operation, only the pins 56 and 78 which are surrounded by the stators 120 and 122 are moved either away from or back towards the rotor 50. The pump supply fitting 34 and outlet supply to column fitting 98 are maintained normally in position except that they are rotated together with the rotation of the rotor 50. The rotor 50 and rotor clamp 54 are rotated around the centerline 100CL by means of drive gear 105.

When the rotor 50 is in its fluid flow position, fluid flows from a separate high pressure pump, through the isolation valve 100, to the sample injector circuit of face seal valve 10, back through another portion of the isolation valve 100, and then to a column.

When the rotor 50 is rotated around centerline 100CL by means of drive gear 105 through an angle of preferably 90°, the pins 56 and 78 are repositioned to the blank fluid flow stop ports 88 and 92 which prevent the flow of fluid and isolate the sample circuit of face seal valve 10 from the remainder of the HPLC system. Those skilled in the art recognize that the drive gear 105 can be either a separate unit from the rotor clamp 54 or else the drive gear 105 can be an integral unitary structure combined with the rotor clamp 54 and even the rotor 50. In addition, although shown as a drive gear, other means known to those skilled in the art such as, for example, an operating handle, can be employed.

Figure 5:
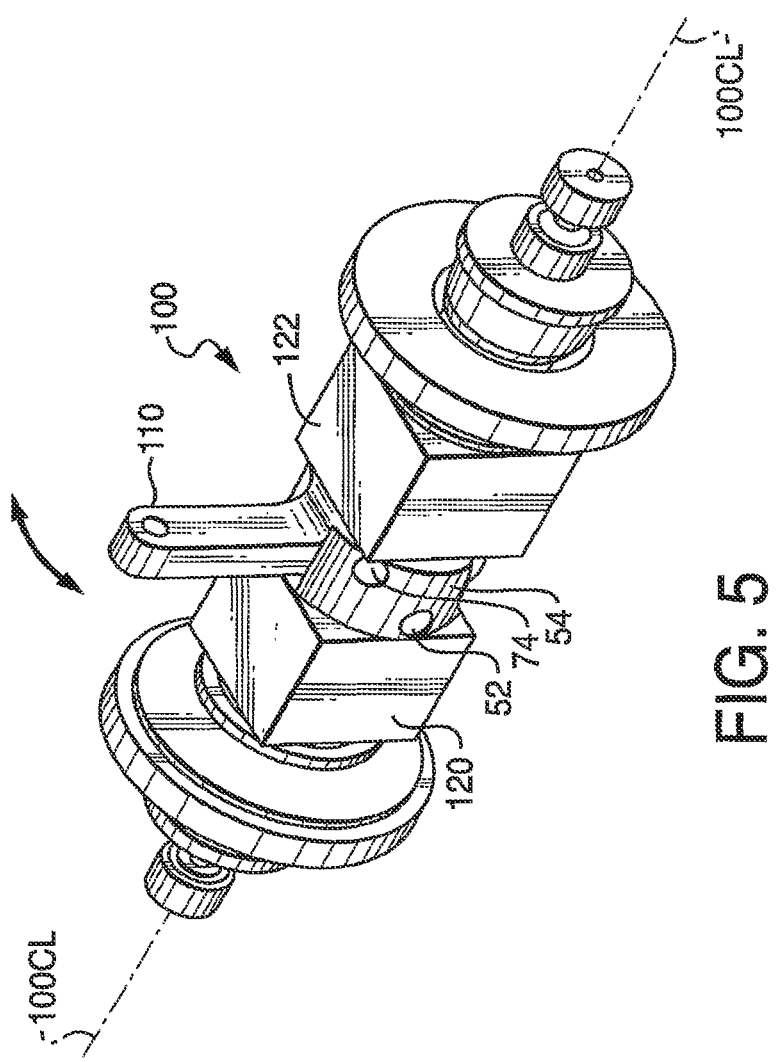
FIG. 5 is a perspective view of a complete embodiment of a second variation of the flow-through isolation valve of the present invention.

FIG. 5 is a perspective view of the complete embodiment of another variation of flow-through isolation valve 100 of the present invention. The rotor 50 is surrounded by rotor clamp 54. The rotor clamp 54 is operated now by a handle 110 that is connected such that the rotor 50 can be rotated around the valve centerline 100CL. Stators 120 and 122 are positioned on opposite ends of the rotor 50.

Figure 5B:
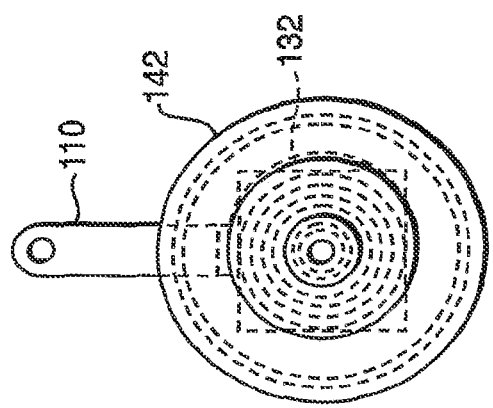
FIG. 5B is an end elevation view of the flow through isolation valve of FIG. 5A.
Figure 5A:
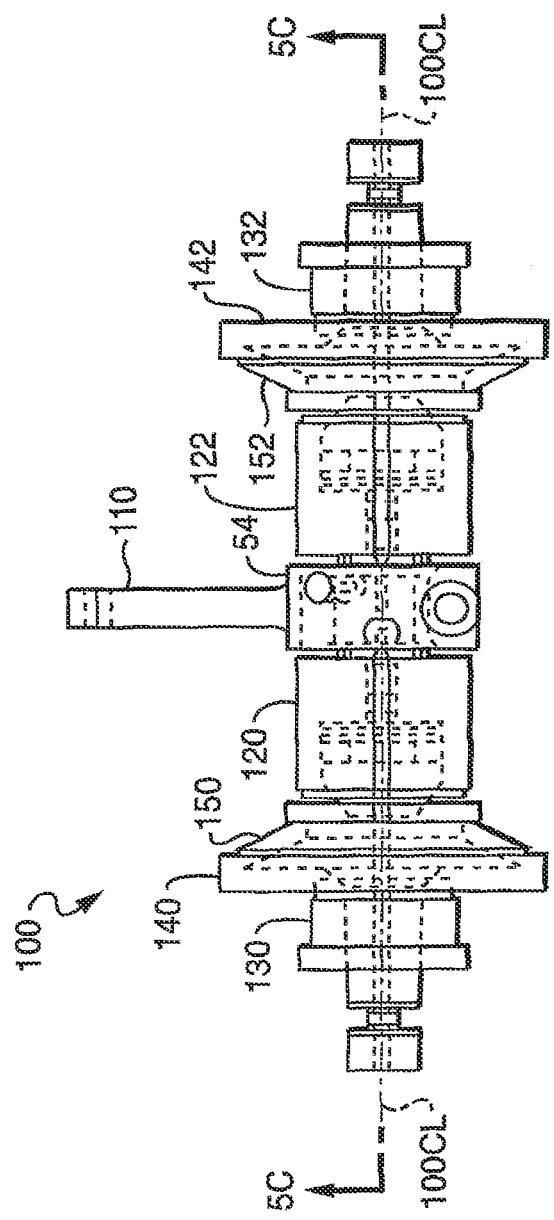
FIG. 5A is a side elevation view of the flow through isolation valve of FIG. 5.

FIG. 5A is a side elevation view of the flow through isolation valve 100 of FIG. 5. The components of valve 100 are centered around centerline 100CL. Specifically, the rotor 50 is positioned so that stators 120 and 122 are disposed on either end of the rotor 50. Belleville springs 150 and 152 deflect the axial loads along the centerline 100CL which act on the rotor 50. The Belleville springs 150 and 152 are mounted on an end of both stators 120 and 122 by means of load washers 140 and 142. The load washers are locked into position by spherical nuts 130 and 132.

FIG. 5B is an end elevation view of the flow through isolation valve 100 of FIG. 5A, which illustrates the spherical nut 132, load washer 142, and rotor handle 110.

Figure 5C:
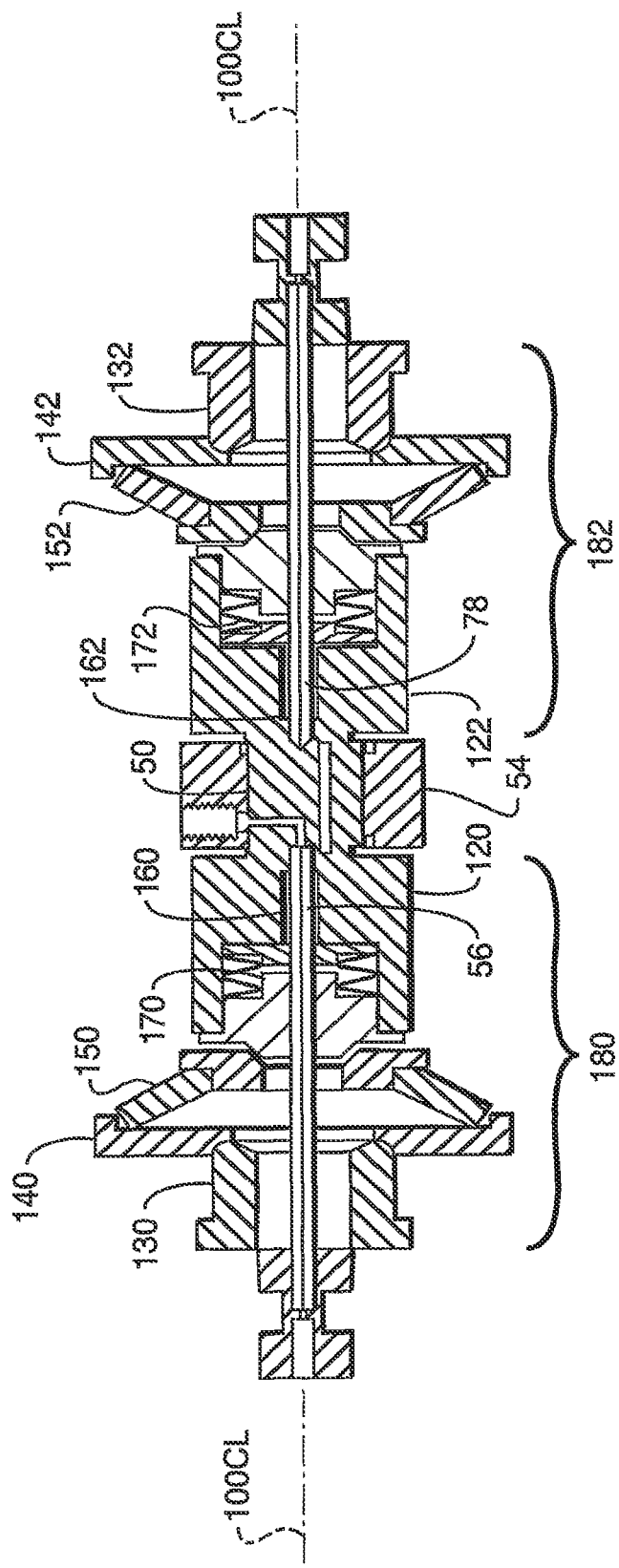
FIG. 5C is a cross-section view taken along the cross-section line 5C-5C' of FIG. 5A.

FIG. 5C is a cross-section view taken along the cross-section line 5C-5C of FIG. 5A. The rotor 50 is sealed by a set of three sealing layers 160 and 162 set around the pins 56 and 78, respectively. The preferred materials for the sealing layers are comprised of PEEK (polyetheretherketone), PTFE (polytetrafluoroethylene), and PEEK. Both sets of sealing layers 160 and 162 are restrained from the axial forces by Belleville spring washers 170 and 172, Belleville springs 150 and 152 and load washers 140 and 142, respectively. The rotor 50 is comprised preferably of PEEK or PEEK blend. The rotor clamp 54 and the stators 120 and 122 are comprised preferably of Type 316 stainless steel.

The respective valve ends 180 and 182 of the flow through isolation valve 100 can be considered to comprise the stators 120 and 122, the sealing layers 160 and 162, Belleville spring washers 170 and 172, Belleville springs 150 and 152, load washers 140 and 142, and spherical nuts 130 and 132.

Figure 6A:
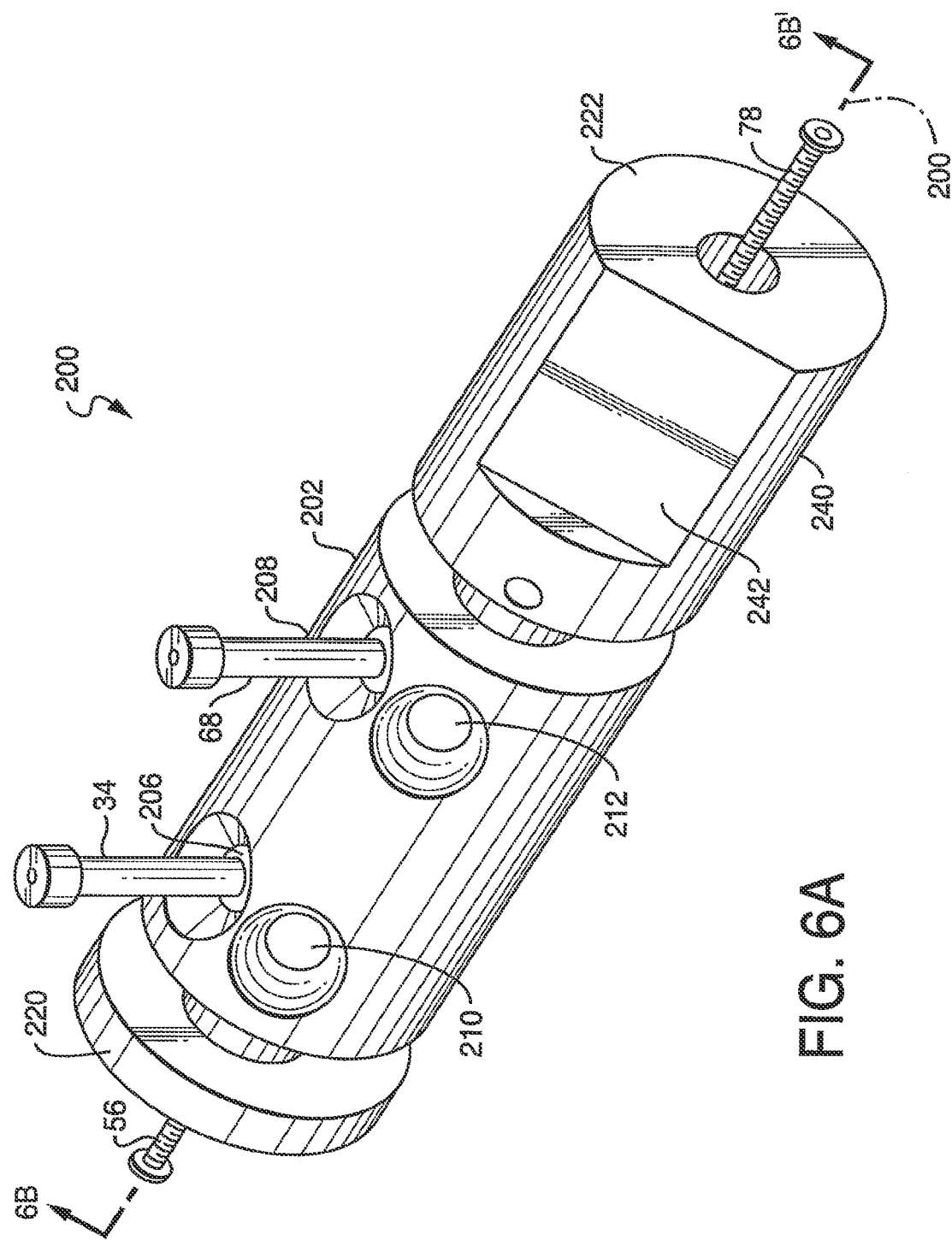
FIG. 6A illustrates a perspective view of a partial second embodiment of a flow-through isolation valve of the present invention.
Figure 6B:
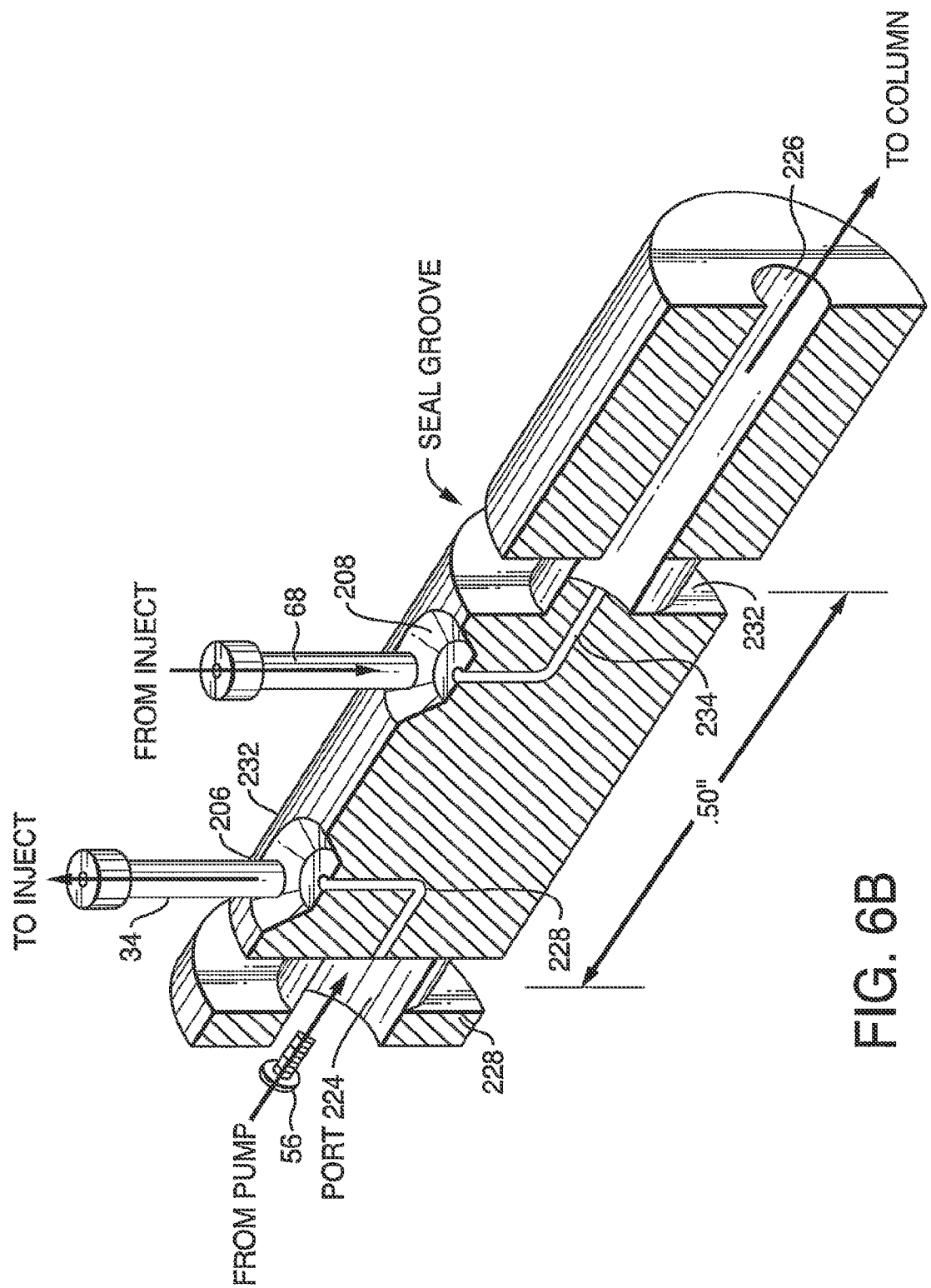
FIG. 6B is a cross sectional perspective view of the partial second embodiment of the present invention as taken along cross-section line 6B-6B' of FIG. 6A.

In a second embodiment as shown in FIG. 6A, a rotor 202 of flow-through isolation valve 200, having an axial centerline 200CL, comprises flow ports 206 and 208 disposed on the outer surface of the rotor 202. FIG. 6B is a cross-sectional view of the flow-through isolation valve 200 taken along the section line 6B-6B' of FIG. 6A. Fluid stop port 210, associated with flow port 206, and fluid stop port 212, associated with flow port 208, are each also disposed on the outer surface of the rotor 202.

As compared to FIGS. 1A to 1C, pump isolation pin valve 34 is now mounted above port 206 of the rotor 202. Column isolation pin valve 68 is now mounted above port 208 of the rotor 202. Port 224 interfaces with port 206 through internal conduit 232 so that during the injection mode, isolation valve pin 34 is in fluidic communication with the pump and face seal valve 10 ports 1 and 2 to sample loop 20.

Correspondingly, port 226 interfaces with port 208 through internal conduit 234 so that during the injection mode, isolation valve pin 68 is 78 are in fluidic communication with the face seal valve 10 ports 5 and 6 from sample loop 20 to the column.

The rotor 202 further comprises an end 240 with a flat surface 242 to enable rotation of the rotor 202 by means of, for example, a drive lever (not shown) or other operating device such as an operating handle known to those skilled in the art.

Those skilled in the art recognize that the isolation valve pins 34 and 68 are positioned to interface with stop ports 210 and 212, respectively, during the load and transition phases and face seal valve 10 is operated in the same way as described for FIGS. 1A and 1B.

Figure 7:
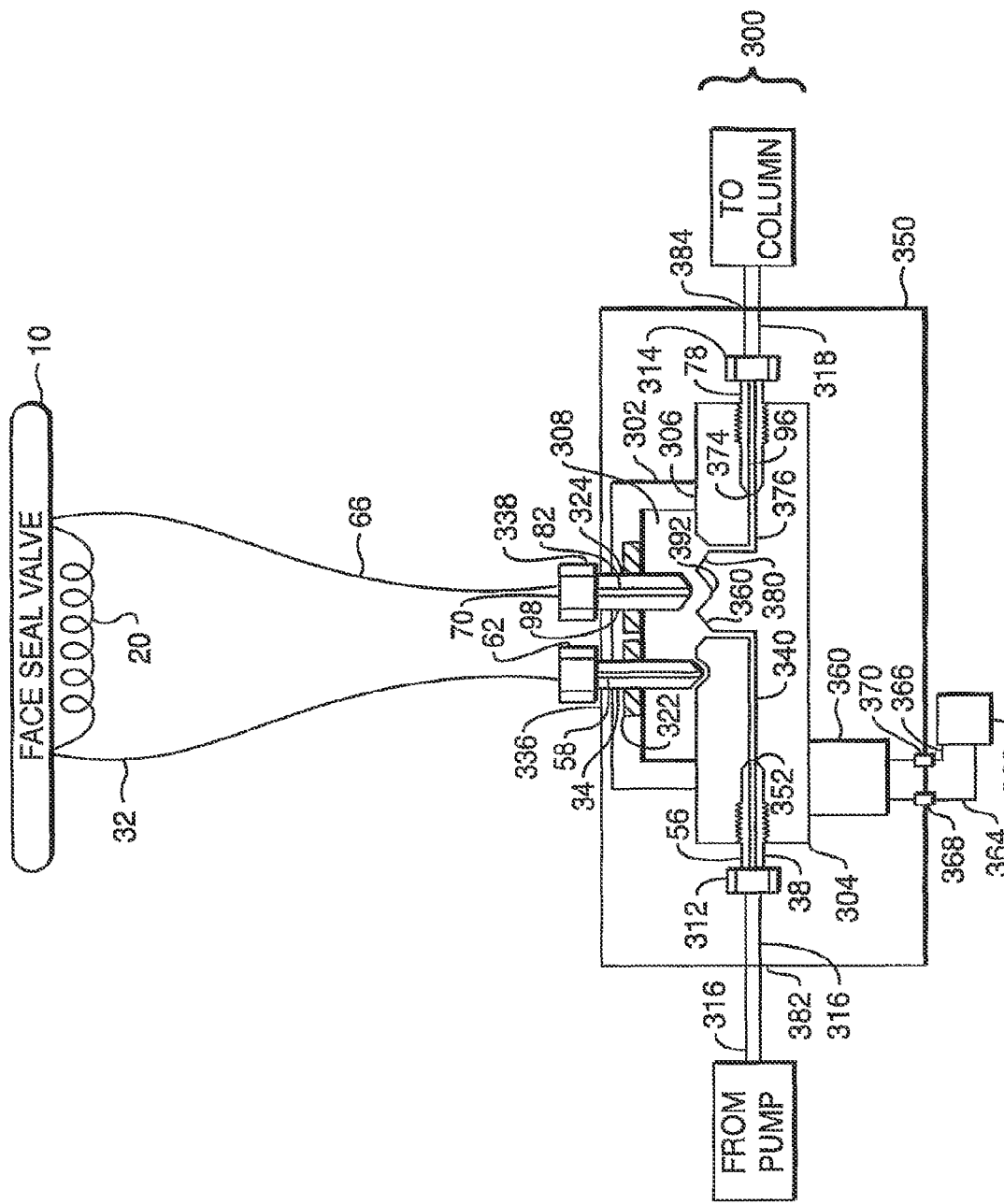
FIG. 7 is a cross sectional elevation view of a third embodiment of the present invention of a linear flow through isolation valve 300 which interfaces with a face seal valve.

FIG. 7 illustrates a an elevation section view of a third embodiment of the present invention of a linear flow through isolation valve 300 which interfaces with face seal valve 10 in the same manner as shown in FIGS. 1A-1C. The linear flow through isolation valve 300 comprises a stationary inner member 302 and a movable inner member 304. The two members 302 and 304 interface at surface 306. The movable member 304 slides along the surface 306 while the stationary member 302 remains in place. This embodiment differs from the first and second embodiments in that pin isolation valve 34 from the high pressure pump (not shown) is inserted into port 322 of the movable member 304 where it is sealed preferably to prevent external leakage by means known to those skilled in the art. Flow is provided from the high pressure pump to the fitting 56 by means of flexible conduit 316 and coupling 312. The internal conduit 38 within the fitting 56 is in fluidic communication with internal conduit 340 within the movable member 304 and with an open port 360 on the interfacing surface 306. The open port 360 is in fluidic communication with a chamber 308 within the stationary member 302 that is bordered by the interfacing surface 306. The stationary member 302 and the movable member 304 act to seal the chamber 308. Isolation valve pin 34 penetrates through stationary member 302 at penetration 322 such that the valve pin 34 can move linearly up and down.

By means of coupling 62, the internal conduit 58 within valve pin 34 is in fluidic communication with conduit tubing 32 to the face seal valve 10. Conduit tubing 66 from the face seal valve 10 is then fluidically coupled to the internal conduit 82 of isolation valve pin 98 by means of coupling 70. Similarly, isolation valve pin 98 penetrates through stationary member 302 at penetration 324 such that the valve pin 98 can move linearly up and down. The internal conduit 82 within isolation valve pin 98 is then in fluidic communication with the chamber 308 within the stationary member 302 that is bordered by the interfacing surface 306. The valve pin 98 is positioned to interface with open port 380 on the interfacing surface 306. The open port 380 is in fluidic communication with the chamber 308.

Those skilled in the art recognize that each of the isolation valve pins 34 and 98 are generally provided with the same valve ends (not shown in FIG. 7) as shown in and as described for FIGS. 5A-5C, previously.

During the injection phase, the internal conduit 82 within the isolation valve pin 98 is in fluidic communication also with internal conduit 376 within the movable member 304 and with an open port 374 on an opposite end of movable member 304. Fitting 78 is inserted into open port 374 so that the internal conduit 96 within fitting 78 is in fluid communication with the sample loop 20 of the face seal valve 10. The internal conduit 96 within the pin fitting 78 is in fluidic communication with the column by means of flexible conduit 318 that is coupled to the fit trig 78 by coupling 314.

During the load phase, the isolation valve pin 98 is positioned to interface with blank port 392 on the surface 306 of movable member 304. Similarly, the isolation valve pin 34 is positioned to interface with blank port 388 on the surface 306 of movable member 304. These actions effectively isolate flow from the high pressure pump to the face seal valve 10 and to the column in the same manner as discussed previously for the first and second embodiments.

To counteract fluid leakage that can occur at the interfacing surface 306 between the stationary member 302 and moving member 304, and also to balance the force tending to separate the stationary member 302 from the moving member 304 due to the pressure within the chamber 308, one means is to provide an outer housing 350 which encloses the stationary member 302 and moving member 304, as well as the fittings 56 and 78. The flexible conduits 316 and 318 can penetrate the outer housing 350 through outer housing penetrations 382 and 384, respectively. With regard to isolation valve pins 34 and 98, either the stators 120 and 122 or the flexible conduit 32 and 66 can be enclosed by outer housing penetrations 336 and 338, respectively. To provide the pressure equalization, the outer housing 350 can be filled with pressurized liquid or gas at a pressure equal to or slightly above the operating pressure of the fluid within the chamber 308.

A means for moving the moving member laterally is provided such as, but not limited to, a linear motor 360 which is coupled to the moving chamber 304 enables the pins 34 and 98 to be shifted between the open ports 360 and 380 and the blank ports 388 and 392, respectively. The linear motor 360 can be supplied electrical power from a power supply 362 with electrical connections 364 and 366 through outer housing penetrations 368 and 370, respectively.

Another variation of the third embodiment is to design the stationary member 302 and the moving member 304 as a duplex or mirror-image design so that the moving member 304 further comprises ports and internal conduits for the pump and column, or a second pump and column, to be capable of serving a second face seal valve simultaneously.

Figure 8:
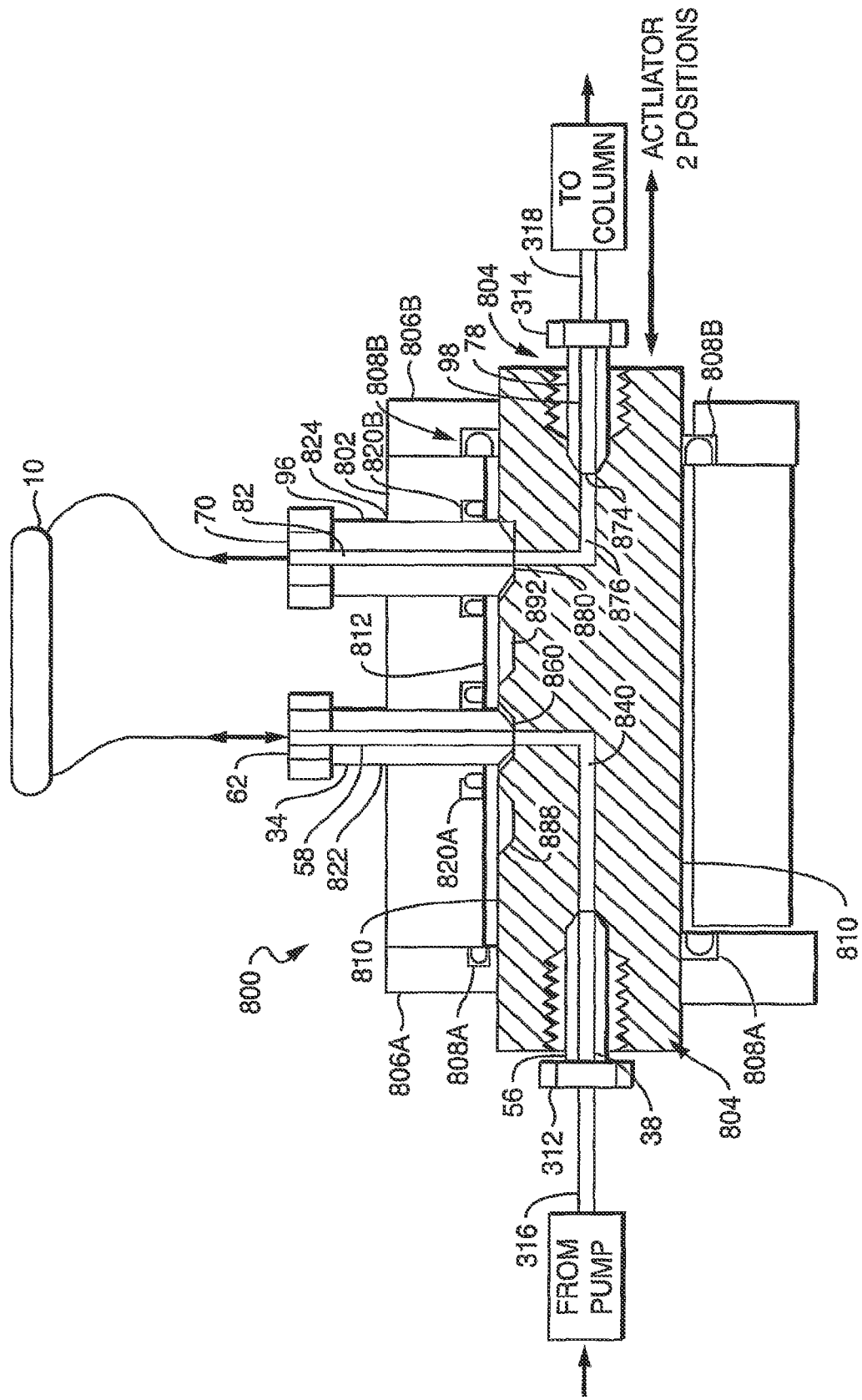
FIG. 8 is a cross sectional elevation view of a fourth embodiment of the present invention of a linear flow through isolation valve which has a configuration similar to the generally cylindrically shaped second embodiment of rotor illustrated in FIGS. 6A and 6B.

In a fourth embodiment, FIG. 8 illustrates linear flow through isolation valve 800 which has a configuration similar to the generally cylindrically shaped second embodiment of rotor 202 illustrated in FIGS. 6A and 6B. As before, the linear flow through isolation valve 800 is comprised of a stationary member 802 and a movable member 804. The movable member 804 is similar to the rotor 202 except that instead of moving in a rotary motion, the movable member 804 moves by sliding linearly through the stationary member 802. The movable member 804 can have any other type of cross-section such as, for example but not limited to, an oval shape or a square with smooth rounded corners. The rotary member 804 is made preferably of either a metal or a polymer or sapphire.

The stationary member 802 is comprised of two surfaces 806a and 806b which surround the movable slider member 804. The two surfaces 806a and 806b each include lip seals 808a and 808b. The stationary member 802 also forms an interfacing surface 810 surrounding the movable member As is the case for the third embodiment, fitting 56 from the high pressure pump (not shown) is inserted into port 352 of the movable member 804 where it is sealed in a manner as to substantially prevent external leakage. Flow is provided from the high pressure pump to the fitting 56 by means of flexible conduit 316 and coupling 312. The internal conduit 38 within the fitting 56 is in fluidic communication with internal conduit 840 within the movable member 804 and with an open port 860 on the interfacing surface 810. The open port 360 is in fluid communication with a volume of space 812 within the stationary member 802 that is bordered by the interfacing surface 810. The volume of space 812 within the stationary member 802 and the movable member 804 are sealed by the end seals 808 and A&B. Isolation valve pin 34 penetrates through stationary member 802 at penetration 822 such that the valve pin 34 can move linearly up and down.

By means of coupling 62, the internal conduit 58 within valve pin 34 is in fluidic communication with conduit tubing 32 to the face seal valve 10 in a similar manner to the third embodiment. Conduit tubing 66 from the face seal valve 10 is then fluidically coupled to the internal conduit 82 of isolation valve pin 96 by means of coupling 70. Similarly, isolation valve pin 96 penetrates through stationary member 802 at penetration 324 such that the valve pin 78 can move linearly up and down. The internal conduit 82 within isolation valve pin 96 is then in fluid communication with the volume of space 812 within the stationary member 802 that is bordered by the interfacing surface 810. The valve pin 96 is positioned to interface with open port 880 on the interfacing surface 310. The open port 880 is in fluidic communication with the volume of space 812.

To seal the isolation valve pins 34 and 96, the stationary member 802 includes self-energized lip seals 820a and 820b, respectively. The lip seals are commercially available from Furon, Inc. of Hoosick Falls, N.Y.

In a similar manner to the third embodiment, during the injection phase, the internal conduit 82 within the isolation valve pin 96 is in fluidic communication also with internal conduit 876 within the movable member 804 and with an open port 374 on an opposite end of movable member 304. Fitting 78 is inserted into open port 874 so that the internal conduit 98 within fitting 78 is in fluid communication with the sample loop 20 of the face seal valve 10. The internal conduit 98 within the fitting 78 is in fluidic communication with the column by means of flexible conduit 318 that is coupled to the fitting 78 by coupling 314.

During the load phase, the isolation valve pin 96 is positioned to interface with blank port 892 on the surface 810 of movable member 804. Similarly, the isolation valve pin 34 is positioned to interface with blank port 888 on the surface 810 of movable member 804. These actions effectively isolate flow from the high pressure pump to the face seal valve 10 and to the column in the same manner as discussed previously for the first and second embodiments.

Although described with respect to application to high pressure fluids, the first, second and third embodiments of the present invention can be applied to fluids at any operating pressure, including sub-atmospheric, i.e., vacuum applications as well.

The invention has been described herein with reference to particular exemplary embodiments. Certain alterations and modifications may be apparent to those skilled in the art, without departing from the scope of the invention. The exemplary embodiments are meant to be illustrative, not limiting of the scope of the invention, which is defined by the appended claims.

What is claimed is:

1. A flow through isolation valve, said flow through isolation valve comprising:
    a stationary member;
    a movable member, a surface of said stationary member interfacing with a surface of said movable member, wherein said movable member includes a plurality of opening formed therein; and
    at least one isolation valve pin;
    said at least one isolation valve pin having a flow through internal conduit and a distal end configured to be inserted into at least one of the plurality of openings formed in the movable member,
    said at least one isolation valve pin being movable relative to said movable member between a first pin position wherein the distal end of the at least one isolation value pin is away from the plurality of opening formed in said movable member and a second pin position wherein the distal end of the at least one isolation valve pin is inserted into one of the plurality of openings formed in said movable member;
    said movable member being movable between (i) a first member position in which said flow through internal conduit is capable of fluidically communicating with at least one blank opening in said movable member and (ii) a second member position in which said flow through internal conduit is capable of fluidically communicating with a flow through conduit in said movable member.

2. The flow through isolation valve according to claim 1, wherein said movable member moves by rotation around an axis of rotation.

3. The flow through isolation valve according to claim 1, wherein said movable member moves by at least one of linear and curvilinear translation.

4. The flow through isolation valve according to claim 1, wherein one of said at least one isolation valve pins is fluidically coupled to a sample loop of a face seal valve of a high pressure liquid chromatography (HPLC) system.

5. The flow through isolation valve according to claim 1, wherein one of said at least one isolation valve pins is fluidically coupled to a pump supplying high pressure liquid to a face seal valve of a high pressure liquid chromatography (HPLC) system.

6. The flow through isolation valve according to claim 1, wherein one of said at least one isolation valve pins is fluidically coupled to a column discharging high pressure liquid from a face seal valve of a high pressure liquid chromatography (HPLC) system.

7. The flow through isolation valve according to claim 1, wherein the distal end of the at least one isolation valve pin is tapered.

8. The flow through isolation valve according to claim 1, wherein the distal end of the at least one isolation valve pin has a truncated cone shape.

9. The flow through isolation valve according to claim 1, wherein at least one of the plurality of openings formed in the movable member has a shape complementary to the distal end of the at least one isolation valve pin.

* * * * *